(12) United States Patent
Lewis, II

(10) Patent No.: US 10,123,960 B2
(45) Date of Patent: Nov. 13, 2018

(54) METHODS FOR TREATING OF SKIN CONDITIONS WITH RETINOID DOUBLE CONJUGATE COMPOUNDS

(71) Applicant: US COSMECEUTECHS LLC, Richmond, VA (US)

(72) Inventor: Joseph A. Lewis, II, Chesterfield, VA (US)

(73) Assignee: PCR TECHNOLOGY HOLDINGS, LC, Richmond, VA (US)

( * ) Notice: Subject to any disclaimer, the term of this patent is extended or adjusted under 35 U.S.C. 154(b) by 68 days.

(21) Appl. No.: 15/036,467

(22) PCT Filed: Nov. 14, 2014

(86) PCT No.: PCT/US2014/065604
§ 371 (c)(1),
(2) Date: May 13, 2016

(87) PCT Pub. No.: WO2015/073769
PCT Pub. Date: May 21, 2015

(65) Prior Publication Data
US 2016/0287507 A1    Oct. 6, 2016

Related U.S. Application Data

(60) Provisional application No. 61/904,532, filed on Nov. 15, 2013.

(51) Int. Cl.
| | |
|---|---|
| *A61K 31/225* | (2006.01) |
| *A61K 8/67* | (2006.01) |
| *A61Q 19/08* | (2006.01) |
| *C07C 403/20* | (2006.01) |
| *A61Q 19/00* | (2006.01) |

(52) U.S. Cl.
CPC .............. *A61K 8/671* (2013.01); *A61Q 19/00* (2013.01); *A61Q 19/08* (2013.01); *C07C 403/20* (2013.01); *C07C 2601/16* (2017.05)

(58) Field of Classification Search
CPC .................... C07C 403/20; C07C 2601/16
USPC ........................................................ 514/547
See application file for complete search history.

(56) References Cited

U.S. PATENT DOCUMENTS

| | | | |
|---|---|---|---|
| 3,920,835 | A | 11/1975 | Van Scott et al. |
| 4,045,559 | A | 8/1977 | Roman |
| 4,053,630 | A | 10/1977 | Yu et al. |
| 4,194,007 | A | 3/1980 | Van Scott et al. |
| 4,216,224 | A | 8/1980 | Van Scott et al. |
| 4,363,815 | A | 12/1982 | Yu et al. |
| 4,603,146 | A | 7/1986 | Kligman |
| 4,829,082 | A | 5/1989 | Shinkai et al. |
| 4,855,463 | A | 8/1989 | Barua et al. |
| 4,877,805 | A | 10/1989 | Kligman |
| 5,093,360 | A | 3/1992 | Yu et al. |
| 5,124,356 | A | 6/1992 | Purcell et al. |
| 5,182,396 | A | 1/1993 | Tachibana |
| 5,605,933 | A | 2/1997 | Duffy et al. |
| 5,652,266 | A | 7/1997 | Bobier-Rival et al. |
| 5,747,051 | A | 5/1998 | Granger et al. |
| 6,180,670 | B1 | 1/2001 | Duffy et al. |
| 2008/0139518 | A1 | 6/2008 | Purcell |

FOREIGN PATENT DOCUMENTS

| | | |
|---|---|---|
| EP | 0391033 A2 | 10/1990 |
| JP | S 5173137 A | 6/1976 |
| JP | S 61207332 A | 9/1986 |
| JP | S 6366160 A | 3/1988 |
| JP | H 04210686 A | 7/1992 |
| JP | H 0780865 B2 | 8/1995 |

*Primary Examiner* — Barbara P Badio
(74) *Attorney, Agent, or Firm* — Leydig, Voit & Mayer, Ltd.

(57) ABSTRACT

A double conjugate molecule made of a retinoid, an organic acid, particularly an a-hydroxy acid, and an alcohol or acyl group, is provided which is useful in treating skin conditions, particularly aging. The retinoid, organic acid, and alcohol/acyl group are preferably linked via ester bonds.

8 Claims, No Drawings

METHODS FOR TREATING OF SKIN CONDITIONS WITH RETINOID DOUBLE CONJUGATE COMPOUNDS

CROSS-REFERENCE TO RELATED APPLICATIONS

This application is a U.S. national stage application under 35 U.S.C. § 371 of International Application No. PCT/US2014/065604, filed on Nov. 14, 2014, and claims benefit to U.S. Provisional Application Ser. No. 61/904,532, filed Nov. 15, 2013, the entire disclosure of which is hereby incorporated by reference herein. The international application was published in English on May 21, 2015, as WO 2015/073769 A1 under PCT Article 21(2).

FIELD

The present invention relates to retinoids, organic acids/alcohols, and alcohols or linked alkyl groups, syntheses and the use of the same in treating skin conditions.

BACKGROUND

Skin is exposed to damage resulting from various sources, including both environmental factors and biochemical processes. Oxidative processes damage proteins, lipids, and other cellular components necessary to maintain the health and appearance of skin, resulting in skin changes, such as skin aging, hyperpigmentation, UV damage, lines, wrinkles, uneven skin texture, etc.

Skin aging is accompanied by a number of morphophysiological changes which are described in the literature. See, e.g., Gilchrest, B. A. *J. Cutaneous Aging Cosmet. Dermatol.* 1988, 1, 1-3, and *Arch. Dermatol.* 1979, 115, 1343-1346. At the physiological level, skin aging is accompanied by a decrease in at least one critical skin function, such as epidermal turnover, healing, clearance of chemicals from the dermis, water regulation, sensory perception, mechanical protection, immunocompetence, vascular reactivity, blood flow, sweat gland function, turgor, sebum production or Vitamin D synthesis.

At the morphological level, a decline in critical physiological functioning is associated with a loss in the normal pattern of corneocyte desquamation, epidermal thinning, and/or the presence of atypical epidermal cells. Other characteristics include a reduction in the height of rete ridges along with a corresponding effacement of dermal papillae, a general weakening of the derma-epidermal junction, excessive accumulation of elastin, and a loss of collagen and other ground substances, a decrease in dermal volume (turgor), pigmentary disorders, attrition of capillary vessels, chronic inflammation and the occurrence of benign, and/or malignant tumors. Some of the clinical manifestations of these morphological changes which are relevant to cosmetic appearance and dermal health include a rough, flaky and/or dry skin surface, itching, excessive wrinkling, sagging, loss of elasticity, sallow color, mottled pigmentation, thinning hair, nail brittleness and, in some cases, skin growths.

The etiological bases underlying skin aging are only partially understood. But, it is recognized that the effect of ultraviolet light (UVL), especially from the sun, constitutes a significant factor in the acceleration of skin aging. Several studies have shown that skin which has been exposed to sunlight undergoes aging sooner than unexposed areas in the same individual. By comparing the histological and functional characteristics of exposed and unexposed skin, investigators have observed differences between chronological and accelerated premature aging. See, e.g., Montagna, W. J. *Inves. Dermatol.* 1979, 73, 47-53; Gilchrest, B. A. *J. Invest. Dermatol.* 1983, 80, 81s-85s; and Gilchrest, B. A. *J. Invest. Dermatol.* 1979, 73, 59-66.

The UVL component of sunlight is responsible for triggering molecular changes that damage biological tissues including the skin. One known mechanism for sun-induced aging results from the generation of free radicals in the skin. One proposed pathway to free radical generation, the so-called Haber-Weiss reaction (shown in Scheme I), is a chemical pathway which generates the most reactive free radical species, the hydroxy radical.

Scheme I

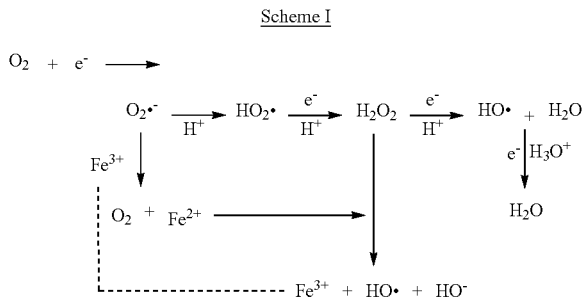

In Scheme I, $O_2 \cdot^-$ is singlet oxygen or the superoxide ion, $HO_2 \cdot$ is the hydroperoxyl radical, $H_2O_2$ is hydrogen peroxide, HO· the hydroxy radical, and $H_2O$ is water. In the Haber-Weiss reaction, electrons ($e^-$) are gained through the oxidation of metals such as iron, copper, and zinc, which are typically present in and on the skin. The hydrogen atoms are gained through the destructive oxidation of biological molecules essential to the normal function of cells, tissues, and organs, such as lipids, proteins, DNA, RNA, and enzymatic cofactors. There are numerous studies showing how the oxidation of these essential biological molecules is detrimental to the skin, in both the long term and short term.

The retinoids are biologically active compounds involved in essential functions such as vision, embryonic development and the growth and maintenance of normal skin. The art teaches that topical application of skin preparations containing retinoids provides a significant improvement in clinical appearance. See, e.g., U.S. Pat. Nos. 4,603,146 and 4,877,805. Additionally, topical application of retinoids provide improvement with respect to several histological parameters, such as thickening of the epidermis including the stratum granulosum, an increase in the height of rete ridges and the number of dermal papillae, a gradual displacement of age-related deposition of dermal elastin by collagen and peptidoaminoglycans, normalization of melanocyte function, and an increase in the number of dermal fibroblasts. See, e.g., Zelickson, A. S. *J. Cutaneous Aging Cosmet. Dermatol.* 1988, 1, 41-47; Weiss, J. S. *JAMA,* 1988, 259, 527-532; Bhawan *J. Arch. Dermatol.* 1991, 127, 666-672; and Kligman, L. H. *Connect. Tissue Res.* 1984, 12, 139-150. U.S. Pat. No. 4,603,146 also describes the use of Vitamin A acid for retarding skin aging, and U.S. Pat. No. 4,877,805 describes the use of retinoids generally for the same purpose. U.S. Pat. No. 5,747,051 describes the use of a retinyl ester for treating a skin condition, though the ester is a simple, single reverse ester compound, such as retinyl palmitate, retinyl acetate, or retinyl propionate, not a double ester or a compound having two or more linking moieties.

The skin is a target for and requires retinoids. This conclusion stems from the fact that Vitamin A deficiencies lead to skin lesions. Additionally, skin cells, such as fibroblasts and keratinocytes, contain high-affinity cytosolic receptors for retinoids, thus further demonstrating the target nature of these skin cells.

It is well-known that therapeutic doses of topically applied retinoids frequently cause skin irritations which interfere with treatment. To solve this problem, the art has resorted to conjugating retinoids with glucuronic acid, among other methods (e.g., microsponge delivery systems or liposomes). See, e.g., U.S. Pat. No. 4,855,463, which discloses water-soluble glucuronic acid derivatives of Vitamin A for improved metabolic uptake; and Chen, S. *J. Invest. Dermatol.* 1992, 98, 560 (Abstract), which describes conjugates of retinoids and acetaminophen. In both cases, conjugation was achieved by attaching the other molecule to carbon-15 of the retinol structure.

U.S. Pat. No. 4,216,224 describes retinyl esters of hydroxy acids, hydroxy amides, or hydroxy acid esters for use in treating psoriasis. U.S. Pat. No. 5,124,356 describes ester and amide conjugates of trans-retinoids, although the molecule conjugated with the retinoid is not described as providing any separate therapeutic benefit. EP 0 391 033 A2 further describes the preparation of retinal derivatives, especially acetals and hemiacetals, useful in treating a variety of skin conditions.

JP S63-66160 A (1988) describes the preparation of a retinoyl ester of 1-ascorbic acid which is taught to be useful for increasing the activity of blood vessel endotheliocyte plasminogen activators, and for increasing the hydrophilic properties of retinol and retinoic acid to reduce instability of the composition due to oxidation. In vitro data on endotheliocyte cultures showed increased activity of plasminogen activator, but no methods or compositions for administration are disclosed.

JP H04-210686 A (1992) describes a method for the manufacture of tocopheryl retinoate. This compound is taught to be useful for treating skin ulcers (e.g., JP S61-207332 A) and for preventing the roughening of skin (e.g., JP S51-73137 A). U.S. Pat. No. 5,182,396 discloses that 1-hydroxy Vitamin D esters with Vitamin A acid are useful for treating cutaneous ulcers and tumors.

Carboxylic acids are also useful in the treatment of aging skin, especially alpha- and beta-hydroxy acids and ketoacids. These are generally referred to as AHAs (Alpha Hydroxy Acids). See, e.g., U.S. Pat. Nos. 3,920,835, 4,045,559, 4,053,630, 4,363,815, and 5,652,266. Additionally, U.S. Pat. No. 4,194,007 describes α-hydroxyretinoic acid and α-ketoretinoic acid as derivatives of retinoic acid.

These AHAs improve the clinical appearance and mechanical properties of aging skin. A normalization in the pattern of epidermal keratinization and a reduction in the cohesive forces acting between keratinocytes and corneocytes have also been reported after treatment with AHAs (Van Scott, E. J. *J. Acad. Dermatol.* 1984, 11, 867-879). Other investigators have observed such benefits as wrinkle reduction after topical application of AHAs. They postulate that AHAs stimulate collagen and glycosaminoglycan synthesis by cultured fibroblasts (Dial, F. D. Cosmetic Dermatology, 1990, 5, 32-34). AHAs also increase the production of collagen and peptidoaminoglycans (Lavker, R. M. *J. Am. Acad. Dermatol.* 1992, 26, 535-544), thereby further improving the general topographical appearance and viscoelastic behavior of skin.

The action by which AHAs improve the clinical appearance and mechanical properties of skin is not thoroughly understood. One feature of aging skin is hyperkeratinization, a condition in which the corneocytes adhere in excess, thereby creating a thickened stratum corneum and a dry appearance. The forces responsible for the adhesion of corneocytes are non-covalent in nature and evidence exists that both ionic and hydrophobic interactions are involved. In the case of ionic interactions, calcium ions are believed to bridge adjacent corneocytes by forming complexation bonds between cholesteryl sulfate residues that are firmly anchored to the corneocyte cell wall (Shapiro, L. J. *Lancet* 1978, 1, 70-72).

Since ionic interactions are pH dependent, AHAs may decrease corneocyte cohesion by temporarily opening up calcium bridges. However, an explanation of activity based on pH alone is not satisfactory. Earlier work aimed at studying the relationship between the chemical structure of these agents and their ability to influence the viscoelastic behavior of the stratum corneum clearly indicates that, among the series of AHAs studied, those having hydroxy groups in the alpha position consistently lowered this parameter (Takahashi, M.; Machida, Y., *J. Soc. Cosmet. Chem.* 1985, 36, 177-187). The lower the viscoelastic modulus, the less force is required to cause deformation (i.e., the softer the stratum corneum).

AHAs are known to produce a long-lasting decrease in the elastic modulus of skin. This means softening and, with regular use, a normalization in the pattern of corneocyte desquamation. Certain beneficial effects have been shown for AHAs conjugated with linear aliphatic chains having eight to ten carbons. See, e.g., Hagan, D. B., et al., "A study of the structure-activity relationships present in skin active agents" *Int'l J. Cosmetic Sci.* 1993, 15, 163-173.

After topical application of an AHA, skin surface pH is temporarily lowered from a normal level of about 5 to a more acidic level of about 3. The localized acidity can result in stinging, particularly on the face where microfissures are more common than on other parts of the body. Charged molecules, such as AHAs, are known to be poor skin penetrators because, ordinarily, they cannot partition and diffuse through the lipid-rich lamellae present in the intercorneocyte spaces. Because charged molecules penetrate the cutaneous barrier very slowly, it may require several hours for the increased surface acidity to be neutralized, which would end the stinging and discomfort to the patient. U.S. Pat. No. 5,605,933 describes that conjugation of a short chain carboxylic acid with a retinoid, can reduce the acidity of residue, but admits that problems relating to irritation, stability, toxicity, and dermal penetration still exist.

The present inventor has found that the formation of a double conjugate unexpectedly improves the moderation of the acidity of known retinoid compounds, including single conjugates. The novel double conjugates of this invention provide an unexpectedly superior treatment by improving AHA rates of percutaneous absorption, improving passage of double conjugates through the intact domains of the stratum corneum, and alleviating acidification of the skin and the accompanying stinging and other discomfort, even when applied to the facial area. By doubly conjugating the retinoid-AHA with a further moiety, e.g., alcohol or acyl group, the problem of skin irritation is unexpectedly significantly addressed.

It will be appreciated that a range of compounds have been considered for the treatment of numerous skin conditions including, inter alia, skin aging, acne, dryness, photodamage, and hyperpigmentation.

SUMMARY

An aspect of the invention provides a molecule of formula (I):

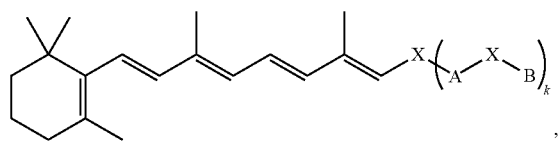

wherein X is independently (CO)O, O(OC), S(O)$_2$O, O(O)$_2$S, (CS)O, O(SC), O—(CH$_2$)$_a$, (CH$_2$)$_a$—O, S—(CH$_2$)$_a$, (CH$_2$)$_a$—S, (CO)N, N(CO), N(O)$_2$S, or S(O)$_2$N, a is 0 or 1, k is 1 or 2, A is a unit of formula (II)

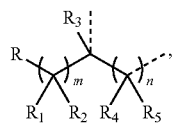

and
B is a unit of formula (III):

$$R_6R_7R_8C— \quad (III),$$

wherein m and n are independently 0, 1, 2, 3, 4, 5, 6, 7, 8, 9, or 10, R, $R_1$, $R_2$, $R_3$, $R_4$, and $R_5$ are independently H, COOH, CHO, alkyl of 1 to 20 carbon atoms optionally substituted or interrupted by one or more OH, N, O, S, P, and/or F, (alk)aryl of 1 to 20 carbon atoms, optionally substituted or interrupted by one or more OH, N, O, S, P, and/or F, or one or more pairs of $R_1$ and $R_2$ or $R_4$, and $R_5$ forms a carbonyl, $R_6$, $R_7$, and $R_8$ are independently H, alkyl of 1 to 20 carbon atoms optionally substituted by OH, CHO, COOR$_9$, CR$_9$OR$_9$, CONR$_9$R$_9$, or (alk)aryl of 1 to 20 carbon atoms optionally substituted by OH, CHO, COOR$_9$, CR$_9$OR$_9$, CONR$_9$R$_9$, and R$_9$ is independently H or an alkyl group of 1 to 6 carbon atoms. Compositions comprising one or more of such molecules, and methods of using and preparing such molecules and/or compositions are also provided by the invention.

DETAILED DESCRIPTION

The invention provides a new class of compounds useful in the treatment of aging skin and to provide methods for the use of such compounds in the treatment of aged and aging skin. Particular benefits achieved by the invention may be increased stability of the active compound, reduced irritation, improved dermal penetration, and a higher therapeutic index (i.e., selectivity, typically defined as TD50/ED50 or LD50/ED50).

The invention provides a class of multi-functional double conjugated retinoids, dimers of a retinoid, and another bioactive ingredient such as an organic acid, preferably a bioactive organic acid, and especially those known generally as AHAs, which are then coupled with a further organic species, generally an alcohol or an acyl group, to thereby form a second connective moiety, such as ester, ether, thioester, thioether, or amide. When used for treating aged skin, these novel double conjugates can provide a high therapeutic index with less accompanying skin irritation that any of the classes of agents known in the art, whether applied individually or in combination.

The invention also provides a pharmaceutical composition which comprises an amount of the novel double conjugate effective to provide a benefit to a morphological and/or clinical aspect of aging skin and a compatible carrier therefor. In a preferred embodiment, the carrier is cosmetically acceptable, if not dermatologically acceptable.

The invention also provides a method for treating aging skin and other skin conditions of a subject, preferably human, having such aged skin, which comprises providing the novel conjugate of this invention as a composition comprising a mixture of the conjugate and a cosmetically acceptable carrier therefor, and applying the composition to the subject such that the amount of conjugate applied is effect to benefit a morphological and/or clinical aspect of the subject's aging, flawed, or damaged skin.

Skin areas subject to treatment, particularly in a subject in need thereof, are the torso, face, eye area, neck, elbow area, knee area, feet, hands, and palms, among others. The invention is particularly useful in the treatment of the facial region, but not limited thereto, and is suited for the body generally.

Among the exemplary conditions subject to treatment, particularly in a subject in need thereof, are acne, dry skin, icthyosis, photodamage, fine lines and wrinkles, hyperpigmentation, anti-aging, loss of skin elasticity and resiliency, loss of extra cellular matrix components in the skin (especially collagen, elastin, and glycosaminoglycans), reduced dermal and epidermal volume (i.e., thinning of the skin), loss of fibroblast activity, sallow complexion, actinic keratoses, and general improvement of skin texture, tone, and clarity of the skin, resulting in more vibrant radiant skin complexion.

Novel double conjugates of retinoids are included in the invention. As used herein, the term "retinoid" includes Vitamin A (retinol) and derivatives such as retinoic acid (e.g., tretinoin, also sold as RETIN-A® brand by Johnson & Johnson Co., New Brunswick, N.J.), retinal (Vitamin A aldehyde), 3,4-didehydroretinol (Vitamin A$_2$), and cosmetically acceptable derivatives thereof, such as other esters or reverse esters (or salts thereof), ethers, aldehydes, alcohols, and the like.

Retinoic acid has a structure of formula (I), shown below:

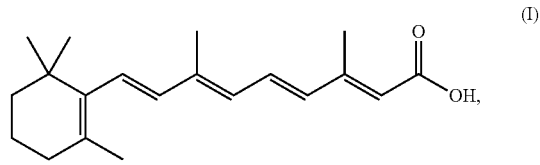 [SMILES: CC1=C(/C=C/C(C)=C/C=C/C(C)=C/C(=O)O)C(C)(C)CCC1]

and the IUPAC name (2E,4E,6E,8E)-3,7-dimethyl-9-(2,6,6-trimethylcyclohex-1-en-1-yl)nona-2,4,6,8-tetraenoic acid. Retinol has the structure of formula (II), shown below:

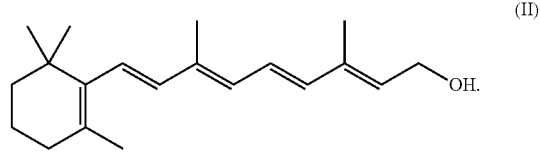 [SMILES: CC1=C(/C=C/C(C)=C/C=C/C(C)=C/CO)C(C)(C)CCC1]

The retinoid of the invention is conjugated with a bioactive agent selected from modified organic acids or alcohols, especially those which are cosmetically acceptable, and particularly those which have a beneficial effect on the appearance and/or properties of aging, flawed, or damaged skin. It is preferred that the retinoid be conjugated with a low molecular weight organic acid ester (i.e., wherein the acid has not more than about 10 carbon atoms). The linkage between the retinoid and the modified organic acid or alcohol may be through an ester, reverse ester, ether, sulfonate ester, reverse sulfonate ester, amide bond, or reverse amide bond, and preferably the linkage is an ester bond. The modified organic acid to which the retinoid is linked has preferably been linked to an alkyl group through an ester, reverse ester, ether, sulfonate ester, reverse sulfonate ester, amide bond, or reverse amide bond, and preferably through an ester bond. After delivery to the dermal tissues, the novel double conjugates are believed to hydrolyze in vivo and yield an active retinoid and active AHA agent. Both the retinoid and the organic acid, and optionally, the hydrolyzed alkyl group, can provide anti-aging, and other cosmetic and/or morphological effects when made available to the skin. It is also possible to link the retinoid to the organic acid or alcohol, then modify the organic acid.

The novel double conjugates of this invention can be made using organic acids or their derivatives, such as aldehydes, ketones, alcohols, esters, reverse esters, anhydrides, acyl halides, and salts thereof, and preferably those which are bioactive (although, in some situations, it may be desirable to provide an organic acid which is relatively inert). The organic acid may comprise from 2 to 24 carbon atoms, from 2 to 18 carbon atoms, from 3 to 12 carbon atoms, from 3 to 10 carbon atoms, from 3 to 6 carbon atoms, and especially 3, 4, or 5 carbon atoms.

Organic acids include α-hydroxy organic acids including, as examples, glycolic, lactic, citric, tartaric, mandelic, benzilic, and malic acids. Particular oxoacids suitable for use with this invention include, for example, glyoxylic and pyruvic acids. Other carboxylic acids, such as pimelic, adipic, glutaric, succinic, fumaric, oxalic, and salicylic acids, are also suitable for use with this invention. Other suitable organic acids include those which are normal cellular constituents. The organic acid may be one or more alpha-hydroxy acids, beta-hydroxy acids, and keto-acids (generally known as AHAs). AHAs generally contain from two to six carbon atoms in their aliphatic residue and are highly ionized and, consequently, strongly acidic.

A general class of such AHA compounds includes α- or β-hydroxy acids containing only one carboxylic group as in formula (III):

R(CR$_1$R$_2$)$_m$(CR$_3$Z)$_n$(CR$_4$R$_5$)$_o$COOH                    (III), wherein
m and o are independently 0, 1, 2, 3, 4, 5, 6, 7, 8, 9, 10, 11, 12, 13, 14, 15, 16, 17, or 18, or any range within,
n is 1, 2, 3, 4, 5, 6, 7, 8, 9, 10, 11, 12, 13, 14, 15, 16, 17, or 18, or any range within,
Z is independently H or OH, and
R, R$_1$, R$_2$, R$_3$, R$_4$, and R$_5$ are independently H, CHO, alkyl of 1, 2, 3, 4, 5, 6, 7, 8, 9, 10, 11, 12, 13, 14, 15, 16, 17, 18, 19, or 20 carbon atoms (or any range within), or (alk)aryl of 5, 6, 7, 8, 9, 10, 11, 12, 13, 14, 15, 16, 17, 18, 19, or 20 carbon atoms (or any range within). Herein, the term (alk)aryl means that an alkyl portion is optionally bonded to the aryl structure, e.g., a benzyl group.

The α- or β-hydroxy acids of this class may be chemically in the form of a straight chain, a ring or a polymer. When in a ring, R and one of R$_1$ or R3 may be omitted from the structure. For example, quinic acid has a structure of (CHOH)$_3$(CH$_2$)$_2$COHCOOH. A relevant oligomer of an α- or β-hydroxy acid is linear lactic acid oligomer containing approximately 3 lactic acid groups.

The α- or β-hydroxy acids may be free acids, peroxides, lactones, amides, esters, or salts formed by reacting the compound with ammonium hydroxide, organic base, or inorganic base. Other representative α- or β-hydroxy acids of this class are: 2-hydroxy-3-methylpentanoic acid, a hydroxy analog of isoleucine; 2,3-dihydroxybutanoic acid, a hydroxy analog of threonine; 2-hydroxy-3-mercaptopropanoic acid, a hydroxy analog of cysteine; 3,3-dithiobis(2-hydroxypropanoic acid), a hydroxy analog of cystine; 2-hydroxy-4-(methylthio)-butanoic acid, a hydroxy analog of methionine; 2-hydroxy-4-(methylsulfoxide)-butanoic acid, another hydroxy analog of methionine; 2-hydroxy-4-(methylsulfonyl)-butanoic acid, still another hydroxy analog of methionine; 2-hydroxy-5-guanidopentanoic acid, a hydroxy analog of arginine; 2,6-dihydroxyhexanoic acid, a hydroxy analog of lysine; 2-hydroxy-6-aminohexanoic acid, another hydroxy analog of lysine; 2,5,6-trihydroxyhexanoic acid, a hydroxy analog of hydroxy lysine; 2,5-dihydroxy-6-aminohexanoic acid, a further hydroxy analog of hydroxy lysine; 2-hydroxy-3-(4-imidazolyl)-propanoic acid, a hydroxy analog of histidine; 2-hydroxy-3-(4-hydroxyphenyl)-propanoic acid, a hydroxy analog of tyrosine; 2-hydroxy-3-(3' indolyl)-propanoic acid, a hydroxy analog of tryptophan; 2-hydroxy-4-mercaptobutanoic acid, a hydroxy analog of homocysteine; 4,4'-dithiobis(2-hydroxybutanoic acid), a hydroxy S analog of homocystine; 2,4-dihydroxybutanoic acid, a hydroxy analog of homoserine; 2-hydroxy-3-sulfinopropanoic acid, a hydroxy analog of cysteine sulfinic acid; 3-aminolactic acid, a hydroxy analog of 3-aminoalanine; 2,4-dihydroxybutanoic acid, a hydroxy analog of 2,4-diaminobutanoic acid; 2-hydroxy-2-methyl-butanoic acid, a hydroxy analog of isovaline; 2,5-dihydroxypentanoic acid, a hydroxy analog of ornithine; 2-hydroxy-5-ureidopentanoic acid, a hydroxy analog of citrulline; 2-hydroxy-6-ureidohexanoic acid, a hydroxy analog of homocitrulline; 2-hydroxy-3-(5'-hydroxyindolyl)propanoic acid, a hydroxy analog of 5-hydroxytryptophan; 3-(3',4'-dihydroxyphenyl)lactic acid, a hydroxy analog of dopa; 3-(3'-iodo-4'-hydroxyl)enyl) lactic acid, a hydroxy analog of 3-iodotyrosine; 3-(3',5'-diiodo-4'-hydroxyphenyl)lactic acid, a hydroxy analog of 3,5-diiodotyrosine; quinic acid; 3-hydroxypropanoic acid; aldonic acids, including trihydroxy butanoic acid, tetrahydroxy-pentanoic acid, pentahydroxyhexanoic acid, and hexahydroxyheptanoic acid; uronic acids, including glyceruric acid, threuric acid, erythreuric acid, xyluric acid, lyxuric acid, arabinuric acid, riburic acid, iduric acid, guluric acid, mannuric acid, altruric acid, alluric acid and taluric acid; 2-hydroxy-3-sulfonopropanoic acid, a hydroxy analog of cysteic acid; 2-hydroxy-3-thio-s-(3'-hydroxy-1',1'-dimethylpropyl) propanoic acid, a hydroxy analog of felinine; p-hydroxyphenylglycolic acid; O-acetylmandelic acid; and O-acetylmandelic acid peroxide.

Since sulfonic acid is an isosteric group relative to carboxylic acid, i.e., having similar steric arrangements and electronic configurations, certain hydroxysulfonic acids may also be included in the above listing. Examples include 2-hydroxymethylsulfonic acid, a hydroxy analog of taurine, 2-hydroxyethylsulfonic acid, and hydroxymethylsulfonic acid, a sulfonic analog of glycolic acid.

Another suitable class of compounds includes α- or β-hydroxy polycarboxylic acids of formula (IV):

$$(CRX)_m(COOH)_n \quad (IV),$$

wherein
X is OH or H when m is at least 2, such that at least one OH is present,
m is 1, 2, 3, 4, 5, 6, 7, 8, 9, or 10,
n is 2, 3, or 4, and
R is independently H, CHO, alkyl of 1, 2, 3, 4, 5, 6, 7, 8, 9, 10, 11, 12, 13, 14, 14, 15, 16, 17, 18, 19, or 20 carbon atoms (or any range within), or (alk)aryl of 5, 6, 7, 8, 9, 10, 11, 12, 13, 14, 15, 16, 17, 18, 19, or 20 carbon atoms (or any range within).

These α- or β-hydroxy polycarboxylic acids may be free acids, peroxides, lactones, amides, esters, or salt forms of either an open chain structure or as a ring form. For example, whereas malic acid is a monohydroxy dicarboxylic acid of an open chain structure, saccharic acid is a tetrahydroxy-dicarboxylic acid of a ring form commercially available as saccharic acid 1,4-lactone. The open chain structure of saccharic acid is also commercially available but as a salt form.

Other representative α- or β-hydroxyacids of this class are: 2-hydroxysuccinamic acid, a hydroxy analog of aspara-gine; 2,2-hydroxyglutaric acid, a hydroxy analog of gluta-mic acid; 2-hydroxyglutaramic acid, a hydroxy analog of glutamine; 2-hydroxy-4-aminoglutaric acid, a hydroxy derivative of glutamic acid; 2,4-dihydroxyglutaric acid, a hydroxy analog of hydroxyglutamic acid; 2,3-dihydroxy-4-aminoglutaric acid, a dihydroxy derivative of glutamic acid; 2-hydroxy-3-thio-s-(1'-carboxy-2'-methylpropyl) propanoic acid, a hydroxy analog of isovalthine; 2-hydroxyadipic acid, a hydroxy analog of 2-aminoadipic acid; 2,6-dihydroxyp-imelic acid, hydroxy analog of 2,6-diaminopimelic acid; 4-hydroxy-4-methylglutamic acid; 3,4-dihydroxyglutamic acid; and aldaric acids, including ribaric acid, arabaric acid, xylaric acid, lyxaric acid, allaric acid, altraric acid, mannaric acid, gularic acid, idaric acid, and talaric acid.

A further suitable class of compounds includes α- or β-ketoacids of formula (V):

$$R_1-CO(CHR_2)_n COOH \quad (V),$$

wherein
n is 0 is 1
$R_1$ and $R_2$ are independently H, CHO, alkyl of 1, 2, 3, 4, 5, 6, 7, 8, 9, 10, 11, 12, 13, 14, 15, 16, 17, 18, 19, or 20 carbon atoms (or any range within) optionally substituted or inter-rupted by one or more OH, N, O, S, P, and/or F, or (alk)aryl of 5, 6, 7, 8, 9, 10, 11, 12, 13, 14, 15, 16, 17, 18, 19, or 20 carbon atoms (or any range within) optionally substituted or interrupted by one or more OH, N, O, S, P, and/or F.

The α- or β-ketoacids may be free acids, lactones, amides, anhydrides, esters, or salt forms of either an open chain structure or as a ring form. Specific examples contemplated here are: acetopyruvic acid; acetyl pyruvic acid; and β-fluo-ropyruvic acid.

A further class of relevant AHA-like compounds (in-cluded as AHAs herein) suitable for certain applications of the invention are the amino acids, including α-, ρ-, γ-, and δ-amino acids, as well as analogs of the AHAs mentioned above, wherein one or more hydroxy groups is replaced by an amine. The natural α-amino acids are preferred, though unnatural analogs and racemates of these or any other AHA mentioned herein are contemplated. Additionally, analogs of the AHAs mentioned above, wherein one or more hydroxy groups is replaced by an thiol, are contemplated for use as an AHA within the meaning of this invention. Also, poly-mers and oligomers of any of the above AHAs may be used in certain embodiments, particularly dimers, trimers, and tetramers, though longer chain analogs, as well as copoly-mers and block copolymers may be used. Alkoxylated forms of AHAs mentioned herein, particularly with ethylene oxide, propylene oxide, and butylene oxides, may be used, e.g., as PEG-1, 2, 3, 4, 5, 6, 7, 8, 9, and 10 analogs at one or more hydroxy groups of the AHA.

Examples of preferred α-hydroxy acids, particularly from two to six carbon atoms, are lactic acid, glycolic acid, malic acid, tartronic acid, tartaric acid, glucuronic acid, pyruvic acid (and its methyl and ethyl esters), 2-hydroxyisobutyric acid, 3-hydroxybutyric acid, citric acid, galacturonic acid, mandelic acid, mucic α-phenyllactic acid, α-phenylpyruvic acid, saccharic acid, α-hydroxybutyric acid, α-hydroxy-isobutyric acid, 3-hydroxybutyric acid, α-hydroxyisocap-roic acid, α-hydroxy-isovaleric acid, atrolactic acid, galac-tanic acid, pantoic acid, glyceric acid, isocitric acid, dihydroxymaleic acid, dihydroxytartaric acid, dihydroxy-fumaric acid, benzylformic acid, and keto-acids of these. Lactic acid is highly preferred, and may be present in its natural, unnatural, or racemic form, but preferably natural. The combination of two or more of any of the above AHAs may be used within the scope of the invention.

Derivatives of organic acids which are suitable in this invention include substitutions on the acid, and especially substitutions at the 2-position (e.g., the α-position of an AHA). Exemplary derivatives include 2-thio derivatives (e.g., wherein the hydroxyl group of the AHA is substituted with a thiol group), thioalkyl and thioalkenyl derivatives (e.g., those substituted at the 2-position of a carboxylic acid, and especially of a hydroxycarboxylic acid), keto deriva-tives, methoxy derivatives, and halogen derivatives (includ-ing F, Cl, Br, and I).

The organic acid may generally be saturated, unsaturated, or polyunsaturated, with double bonds independently in cis- or trans-configurations. Further, the organic acid can be straight- or branched-chain, substituted or unsubstituted, acyclic, cyclic, or heterocyclic, and including aromatic com-pounds. Also generally suitable are organic acids which are liquid at ambient pressure and temperature (i.e., about 25° C. and 1 atm).

The second conjugating element is generally an alcohol, diol, or polyol, with a 1 to 20 carbon atoms. A relevant alcohol may have 1, 2, 3, 4, 5, 6, 7, 8, 9, 10, 11, 12, 13, 14, 15, 16, 17, 18, 19, or 20 carbon atoms, preferably, any range within. The second conjugating element may include com-pounds of formula (VI):

$$(R_1X)_1 Y \quad (VI),$$

wherein
1 is 1, 2, or 3,
X is H or independently OH when the total number of carbons is at least 2,
Y is COH, COOH, $CONH_2$, or $SO_3H$,
$R_1$ is independently H, CHO, $COOR_4$, $COR_4$, $CONR_4R_4$, alkyl of 1, 2, 3, 4, 5, 6, 7, 8, 9, 10, 11, 12, 13, 14, 15, 16, 17, 18, 19, or 20 carbon atoms (or any range within), or (alk)aryl of 5, 6, 7, 8, 9, 10, 11, 12, 13, 14, 15, 16, 17, 18, 19, or 20 carbon atoms (or any range within), where the alkyl and/or (alk)aryl is optionally substituted by CHO, $COOR_4$, $COR_4$, $CONR_4R_4$, and
$R_4$ is independently an alkyl group of 1, 2, 3, 4, 5, or 6 carbon atoms (or any range within).

Specific examples of the second conjugating element are methanol, ethanol, propanol, isopropanol, n-butanol, any s-butanol, isobutanol, tert-butanol, n-pentanol, 2-pentanol, 3-pentanol, 2-methylbutanol, 3-methylbutanol, 2-methylbutan-2-ol, 3-methylbutan-2-ol, and neopentanol, as well as mono ether diols, such as ethylene glycol monomethyl ether, ethylene glycol monoethyl ether, ethylene glycol monobutyl ether, propylene glycol monomethyl ether, propylene glycol monoethyl ether, propylene glycol monobutyl ether, diethylene glycol monomethyl ether, and diethylene glycol monoethyl ether. Particular preference is given to ethanol. Specific diols useful as the second conjugating element are ethylene glycol, 1,3-propanediol, 1,2-propanediol, 1,4-butanediol, 1,3-butanediol, 2,3-butanediol, 1,2-butanediol, 1,5-pentanediol, 2,4-pentanediol, 2,3-pentanediol, 1,4-pentanediol, and 1,2-pentanediol. Specific exemplary polyols include sugars, glucosamine, and glycerine. Esters, such as acetates and propionates of the diols and polyols may be used, and the diols or polyols may be alkoxylated in the same manner discussed for the AHAs.

The second conjugating element may also be an acyl moiety, depending on the directional orientation of the linking of the retinoid to the organic acid (AHA). Exemplary variants, named as conjugate bases, may be acetate, propionate, isobutyrate, butyrate, 2-methylbutyrate, 3-methylbutyrate, pivalate, valerate, 2-methylpentanoate, 2-ethylpentanoate, 3-methylpentanoate, 3-ethylpentanoate, and 4-methylpentanoate. Preferred acyl groups are acetate, propionate, isobutyrate, and butyrate.

The second conjugating element may be saturated, unsaturated, or polyunsaturated, with double bonds independently in cis- or trans-configurations. The second conjugating element can be straight-chained or branched, substituted or unsubstituted, acyclic, cyclic, or heterocyclic, and including aromatic compounds. Suitable second conjugating elements are generally liquid at ambient pressure and temperature (i.e., about 25° C. and 1 atm).

The linking moieties connecting the retinoid, AHA, and alkyl skeleton may independently be (reverse) esters, ethers, (reverse) amides, (reverse) sulfonates, (reverse) sulfonamides, sulfides, (reverse) thioesters, (reverse) thioates, (reverse) dithioates, in any order or combination. For example, embodiments of the invention may include double conjugates having two esters, a reverse ester and an ester, two reverse esters, an ester and a reverse ester, an ester and a sulfonate, a reverse ester and a sulfonate, two sulfonates, two reverse sulfonates, a sulfonate and a reverse sulfonate, an ester and an amide, a reverse sulfonate and an ester, a reverse sulfonate and an amide, etc. Any synthesizable linkage combination may be used, especially pharmaceutically compatible and less odorous compounds. The double conjugate preferably is hydrolyzable under natural conditions. Adjusting the rate of hydrolysis is an aspect of this invention.

An embodiment of the invention provides a double conjugate ester from first reacting an AHA, preferably lactic acid, with an alcohol, preferably ethanol, to produce a single conjugate acid—ester (e.g. Ethyl Lactate), and, second, reacting the single conjugate AHA ester with retinoic acid to produce a double conjugate acid-ester (e.g., ethyl lactate retinoate). This embodiment eliminates substantially all to all acidity in the final molecule, relative to a single conjugate of an AHA with a retinoid, such as lactyl retinoate (2-(((2E,4E,6E,8E)-3,7-dimethyl-9-(2,6,6-trimethylcyclohex-1-en-1-yl)nona-2,4,6,8-tetraenoyl)oxy)propanoic acid). This embodiment can also reduce the irritation potential relative the single conjugate option (e.g., lactyl retinoate) and improving the skin penetration and effectiveness.

Embodiments of the invention include compositions comprising 0.01 to 0.1, 0.15, or 0.2 wt % double conjugates of retinoic acid with a lactate ester, wherein the lactic acid ester is ethyl, methyl, propyl, isopropyl, butyl, isobutyl, t-butyl, or benzyl. The lactate residue in these embodiments may be enantiomerically pure R or S, e.g., with an enantiomeric excess (e.e.) of 75, 90, 95, 98, 99, 99.5, 99.9, or 99.99, or it may be a racemate. Any of the chiral AHA residues in the double conjugate herein described may likewise be enantiomerically pure R or S, e.g., with an e.e. of 75, 90, 95, 98, 99, 99.5, 99.9, or 99.99, or may be a racemate.

An aspect of the invention provides a molecule of formula (I):

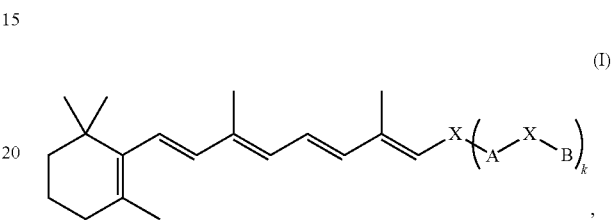

(I)

wherein X is independently (CO)O, O(OC), S(O)$_2$O, O(O)$_2$S, (CS)O, O(SC), O—(CH$_2$)$_a$, (CH$_2$)$_a$—O, S—(CH$_2$)$_a$, (CH$_2$)$_a$—S, (CO)N, N(CO), N(O)$_2$S, or S(O)$_2$N, a is 0 or 1, k is 1 or 2, A is a unit of formula (II)

(II)

and
B is a unit of formula (III):

R$_6$R$_7$R$_8$C—  (III), wherein m and n are independently 0, 1, 2, 3, 4, 5, 6, 7, 8, 9, or 10, R, R$_1$, R$_2$, R$_3$, R$_4$, and R$_5$ are independently H, COOH, CHO, alkyl of 1 to 20 carbon atoms optionally substituted or interrupted by one or more OH, N, O, S, P, and/or F, (alk)aryl of 1 to 20 carbon atoms, optionally substituted or interrupted by one or more OH, N, O, S, P, and/or F, or one or more pairs of R$_1$ and R$_2$ or R$_4$, and R$_5$ forms a carbonyl, R$_6$, R$_7$, and R$_8$ are independently H, alkyl of 1 to 20 carbon atoms optionally substituted by OH, CHO, COOR$_9$, CR$_9$OR$_9$, CONR$_9$R$_9$, or (alk)aryl of 1 to 20 carbon atoms optionally substituted by OH, CHO, COOR$_9$, CR$_9$OR$_9$, CONR$_9$R$_9$, and R$_9$ is independently H or an alkyl group of 1 to 6 carbon atoms.

A further aspect of the invention provides the above molecule, wherein X is independently (CO)O, O(OC), O—(CH$_2$)$_a$, (CH$_2$)$_a$—O, (CO)N, or N(CO); a is 0 or 1; k is 1 or 2; m is 0, 1, 2, 3, 4, 5, 6, or 7; n is 0, 1, 2, or 3; R, R$_1$, R$_2$, R$_3$, R$_4$, and R$_5$ are independently H, COOH, CHO, alkyl of 1 to 15 carbon atoms optionally substituted by one or more OH or interrupted by one or more O, (alk)aryl of 1 to 15 carbon atoms, optionally substituted by one or more OH or interrupted by one or more O, or one or more pairs of R$_1$ and R$_2$ or R$_4$, and R$_5$ forms a carbonyl; R$_6$, R$_7$, and R$_8$ are independently H, alkyl of 1 to 15 carbon atoms optionally substituted by OH, CHO, COOR$_9$, CR$_9$OR$_9$, or CONR$_9$R$_9$, or (alk)aryl of 1 to 15 carbon atoms optionally substituted by OH, CHO, COOR$_9$, CR$_9$OR$_9$, or CONR$_9$R$_9$; and R$_9$ is independently H or an alkyl group of 1 to 5 carbon atoms.

A further aspect of the invention provides the above molecule, wherein X is independently (CO)O, O(OC), O—(CH$_2$)$_a$, or (CH$_2$)$_a$—O; a is 0 or 1; k is 1; m is 0, 1, 2, or 3; n is 0 or 1; R, R$_1$, R$_2$, R$_3$, R$_4$, and R$_5$ are independently H, COOH, CHO, alkyl of 1 to 10 carbon atoms optionally substituted by one or more OH or interrupted by one or more O, (alk)aryl of 1 to 7 carbon atoms, optionally substituted by one or more OH or interrupted by one or more O, or one or more pairs of R$_1$ and R$_2$ or R$_4$, and R$_5$ forms a carbonyl; R$_6$, R$_7$, and R$_8$ are independently H, alkyl of 1 to 10 carbon atoms optionally substituted by OH, CHO, COOR$_9$, CR$_9$OR$_9$, CONR$_9$R$_9$, or (alk)aryl of 1 to 7 carbon atoms optionally substituted by OH, CHO, COOR$_9$, CR$_9$OR$_9$, CONR$_9$R$_9$; and R$_9$ is independently H or an alkyl group of 1 to 4 carbon atoms.

A further aspect of the invention provides the above molecule, wherein X is independently (CO)O, O(OC), O—(CH$_2$)$_a$, or (CH$_2$)$_a$—O; a is 0 or 1; k is 1; m is 0; n is 0 or 1; R, R$_1$, R$_2$, and R$_3$ are independently H, alkyl of 1 to 8 carbon atoms optionally substituted by one or more OH, or (alk)aryl of 1 to 7 carbon atoms optionally substituted by one or more OH; R$_6$, R$_7$, and R$_8$ are independently H, alkyl of 1 to 8 carbon atoms optionally substituted by OH, COOR$_9$, CR$_9$OR$_9$, or (alk)aryl of 1 to 8 carbon atoms optionally substituted by OH, COOR$_9$, CR$_9$OR$_9$; and R$_9$ is independently an H or alkyl group of 1 to 3 carbon atoms.

A further aspect of the invention provides the above molecule, having a formula (Ib)

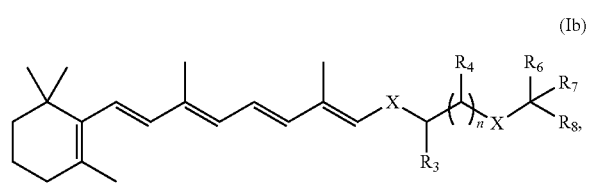

wherein X is independently (CO)O, O(OC), O—(CH$_2$)$_a$, or (CH$_2$)—O; a is 0 or 1; n is 0 or 1; R$_3$, and R$_4$ are independently H or alkyl of 1 to 5 carbon atoms optionally substituted by one or two OH; R$_6$, R$_7$, and R$_8$ are independently H or alkyl of 1 to 5 carbon atoms optionally substituted by OH, COOR$_9$, or CR$_9$OR$_9$; and R$_9$ is independently an H or alkyl group of 1 to 3 carbon atoms.

A further aspect of the invention provides the above molecule, having a formula (Ic)

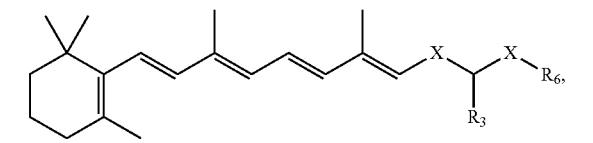

wherein X is independently (CO)O, O(OC), (O—CH$_2$)$_a$, or (CH$_2$)$_a$—O; a is 0 or 1; R$_3$ is H or alkyl of 1, 2, 3, 4, or 5 carbon atoms optionally substituted by one or two OH; R$_6$ is alkyl of 1, 2, 3, 4, or 5 carbon atoms optionally substituted by OH, COOR$_9$, or CR$_9$OR$_9$; and R$_9$ is independently an H or alkyl group of 1, 2, or 3 carbon atoms.

A further aspect of the invention provides the above molecule, having a formula (Id)

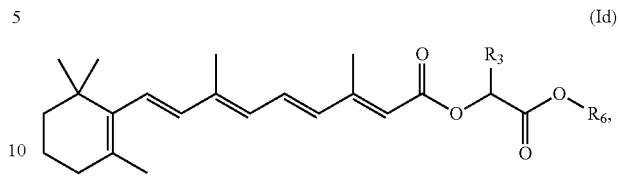

wherein R$_3$ is H or alkyl of 1, 2, 3, 4, or 5 carbon atoms; and R$_6$ is alkyl of 1, 2, 3, or 4 carbon atoms.

A further aspect of the invention provides the above molecule (Id), wherein R$_3$ is alkyl of 1, 2, or 3 carbon atoms; and R$_6$ is alkyl of 1, 2, or 3 carbon atoms.

A further aspect of the invention provides the above molecule (Id), wherein R$_3$ is alkyl of 1 or 2 carbon atoms; and R$_6$ is alkyl of 1, 2, or 3 carbon atoms.

A further aspect of the invention provides the above molecule (Id), wherein R$_3$ is alkyl of 1 carbon atom; and R$_6$ is alkyl of 2 or 3 carbon atoms.

A further aspect of the invention provides the above molecule, having a formula (Ie)

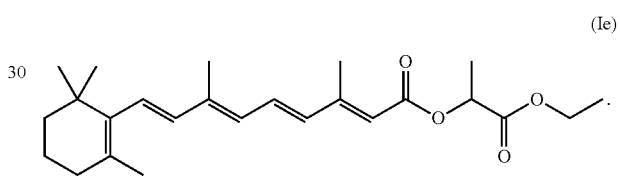

A further aspect of the invention provides the above molecule, having a formula (If)

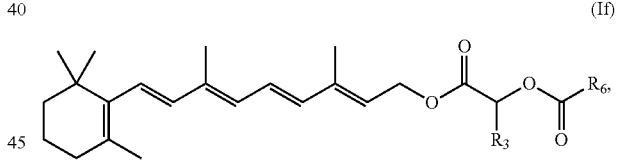

wherein R$_3$ is H, COOH, alkyl of 1, 2, 3, 4, or 5 carbon atoms; R$_6$ is alkyl of 1, 2, 3, or 4 carbon atoms.

A further aspect of the invention provides the above molecule (If), wherein R$_3$ is alkyl of 1, 2, 3, or 4 carbon atoms; and R$_6$ is alkyl of 1, 2, or 3 carbon atoms.

A further aspect of the invention provides the above molecule (If), wherein R$_3$ is alkyl of 1, 2, or 3 carbon atoms; and R$_6$ is alkyl of 1 or 2 carbon atoms.

A further aspect of the invention provides the above molecule, having a formula (Ig)

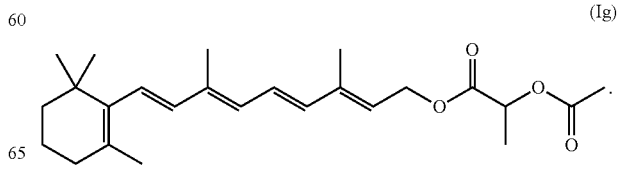

A further aspect of the invention provides a composition, comprising: a carrier; and 0.0001 to 5 wt. % of the above molecule, relative to a total weight of the composition.

A further aspect of the invention provides the above composition, further comprising an α-hydroxy acid.

A further aspect of the invention provides a method, comprising: coupling a retinoid compound with a first organic acid or alcohol; and coupling the first organic acid or alcohol with a second organic alcohol or acid, in an arbitrary order, to obtain the above molecule, wherein, in the molecule, the retinoid compound is covalently bonded to the first organic acid or alcohol, and wherein, in the molecule, the first organic acid or alcohol is covalently bonded (i) to the second organic alcohol or acid, and (ii) to the retinoid.

A further aspect of the invention provides a method of treating a skin condition in a human, comprising: contacting the skin of the human in need of such treatment with an effective amount of the above molecule, wherein the skin condition is aging, acne, dryness, photodamage, hyperpigmentation, icthyosis, fine lines and wrinkles, loss of skin elasticity, loss of skin elasticity resiliency, loss of extra cellular matrix components in the skin, reduced dermal volume, reduced epidermal volume, loss of fibroblast activity, sallow complexion, actinic keratoses, or a combination thereof.

A further aspect of the invention provides the above method, wherein the treating reduces skin irritation relative to administering a single conjugate ester of a retinoid covalently bonded to an α-hydroxy acid.

A further aspect of the invention provides the above method, wherein the treating increases penetration into the skin and has increased efficacy relative to administering a single conjugate ester of a retinoid covalently bonded to an α-hydroxy acid.

Further inventive double conjugates are of formula (VII):

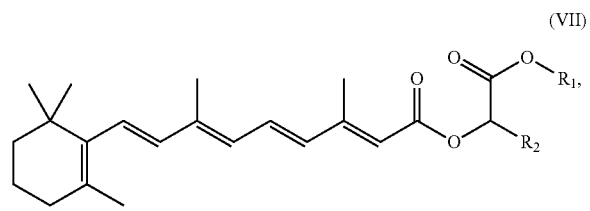

(VII)

wherein $R_1$ and $R_2$ are independently a linear, branched, or ring alkyl group with 1, 2, 3, 4, or 5 carbons, optionally substituted by one or two hydroxy groups. A preferred double conjugate is the compound of formula (VIII):

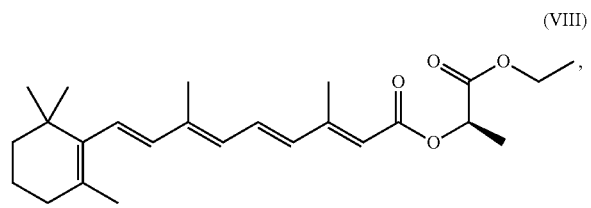 [SMILES: CCOC(=O)[C@@H](C)OC(=O)/C=C(C)/C=C/C=C(C)/C=C/C1=C(C)CCCC1(C)C]

(VIII)

though racemates and unnatural conformations of the same could be preferable in some applications.

Inventive formulations containing the double conjugate may further contain additional free or esterified AHAs, particularly lactic acid. A cosmetically acceptable organic acid, especially one or more AHAs, can optionally be present independently in the composition in an amount, preferably a bioactively effective amount, such as 0.001 to 20 wt. %, relative to the total weight of the composition, or preferably 0.01 to 10 wt. %, 0.01 to 5.0 wt. %, 0.01 to 1 wt. %, 0.01 to 0.5 wt. %, 0.01 to 0.25 wt. %, or 0.01 to 0.15 wt. %. When one or more such organic acids or AHAs are present in inventive compositions, the pH of the composition may need to be raised to more neutral levels by the addition of an alkaline material (e.g., sodium, potassium, or ammonium hydroxide).

The synthesis of the initial conjugates of this invention may require conjugating the lipophilic retinoid with a lipophobic molecule such as any of the AHAs. Conjugates having ester or even ether linkages may be hydrolyzed in water, thereby making synthesis more difficult. Accordingly, it can be beneficial if not desirable to protect active moieties on the AHA conjugated with the retinoid, or the retinoid and/or AHA individually. This precaution can facilitate the formation of a conjugate bond and/or solubilizing both of the reactants (retinoid and AHA) in a common medium. The double conjugate may be formed either (1) by first forming an ester, ether, amide, thioester, etc., of the AHA, then coupling the modified AHA to the optionally protected retinoid; or (2) coupling the optionally protected AHA to the optionally protected retinoid, then forming ester, ether, amide, thioester, etc., on the AHA. One or more deprotecting or protecting steps may be useful in either synthesis route, (1) or (2).

In various syntheses of double conjugates within the scope of this invention, it may be necessary to protect one or more reactive groups, such as hydroxy, amine, or mercapto groups. Exemplary protecting groups are detailed in *Greene's Protective Groups in Organic Synthesis* (4$^{th}$ Ed., Hoboken: Wiley, 2007), which is incorporated herein in its entirety by reference. Such methods of protection for particular substituents are known to those skilled in the arts of organic synthesis.

In practicing the present invention, it should be appreciated that double conjugate formation may require a precursor or derivative of the organic acid required for the synthesis. The skilled artisan can readily choose a synthesis scheme and a suitable precursor or derivative for the production of the desired double conjugate.

In preparing a composition for use in treating skin conditions, one or more double conjugates (which are chemically compatible) are provided in a cosmetically or pharmaceutically acceptable vehicle. The amount of the double conjugate may range between about 0.0001% and 5% by weight, based on the total weight of the composition comprising the double conjugate. In certain applications, the amount of double conjugate may be 0.001 to 1.0 wt. %, while further embodiments may use 0.01 to 0.75 wt. % or 0.01 to 0.25 wt. % of the double conjugate. Certain applications may, however, require the amount of double conjugate within the range of 0.0001 to 5 wt. % to have a weight content endpoint (either upper or lower end of the range) of 4, 3.5, 3, 2.75, 2.5, 2.25, 2, 1.75, 1.5, 1.25, 1.1, 1.05, 1.0, 0.95, 0.9, 0.85, 0.8, 0.75, 0.7, 0.65, 0.6, 0.55, 0.5, 0.45, 0.4, 0.35, 0.3, 0.25, 0.2, 0.175, 0.15, 0.125, 0.1, 0.075, or 0.05 wt. %. Fractions of 0.025 and/or 0.01 may be added to any of the foregoing endpoints. For lower content range formulations, contemplated for longer term use, content endpoints (upper or lower) within 0.0001 to 0.15 wt. % may be 0.15, 0.14, 0.13, 0.125, 0.12, 0.115, 0.11, 0.105, 0.1, 0.09, 0.08, 0.07, 0.06, 0.05, 0.04, 0.03, 0.02, 0.01, 0.005, or 0.001 wt. %. Again, fractions of 0.005, 0.0025, and/or 0.001 may be added to any of the foregoing endpoints. The composition may be applied between one and three times each day to an affected area, though some applications contemplate hourly or semi-hourly use. The content of double conjugate is generally dependent upon the duration of the contemplated application of the composition. For example, an embodiment containing 1.0 wt. % double conjugate within the composition may be applied for less than 10 minutes, or even 3 or fewer minutes. For more concentrated embodiments, e.g., 2.5 wt. %, application times of less than 1 minute, and even 10-20 seconds are contemplated.

Suitable vehicles or carriers for storage and/or delivery of the novel double conjugates of this invention may in liquid, ointment, salve, spray, poultice, or other forms, and will preferably have a lipophilic character. Suitable carriers include petrolatum, triglycerides, various esters, fatty alcohols, alkylene glycols, and ethanol, of which polypropylene glycol, and polyethylene glycol are most preferred. Compatible combinations of these carriers are also suitable.

Carrier systems for topical delivery include cleansers, lotions, ointments, salves, serums, creams, gels, foams, sprays (both mists and aerosols), patches, and masks. The carriers are present as needed for the desired delivery system. Additional components may be added according to conventional practice. For example, the final composition may contain various colorants, fragrances, thickeners (such as xanthan gum), preservatives, humectants, surfactants, and dispersants, including typical botanical extracts such as those derived from witch hazel or chamomile (e.g., those having an astringent, antiseptic, or other desired effect). The composition may likewise include a penetration enhancer such as dimethyl sulfoxide (DMSO). It may also include one or more additional active ingredients (such as an antibiotic, anesthetic, or growth factor).

Cosmetic and dermatological compositions of the invention can exist in various forms. For example, the compositions of the invention can be in the form of a cream, a solution, a serum, an anhydrous preparation, an emulsion or microemulsion of the type water-in-oil (W/O) or of the type oil-in-water (O/W), a multiple emulsion, for example of the type water-in-oil-in-water (W/O/W), a gel, a solid stick, an ointment or an aerosol. It may be advantageous to administer a composition within the invention in matrix, e.g., in collagen matrices, encapsulated in cellulose, in gelatin, in wax matrices, or as a liposomal encapsulation. Preferably the composition of the invention is in the form of a cream. It is also possible and advantageous within the scope of the present invention to add a composition of the invention to aqueous systems or surfactant compositions for cleansing the skin.

Emulsions according to the present invention are advantageous and contain, for example, the afore-mentioned fats, oils, waxes, and other adipoids, and water and an emulsifier, as is used conventionally for such a type of formulation.

The lipid phase can advantageously be selected from the following substance group: mineral oils, mineral waxes; oils, such as triglycerides of capric or caprylic acid, also natural oils, such as for example castor oil; fats, waxes and other natural and synthetic adipoids, preferably esters of fatty acids with alcohols of low carbon number, for example with isopropanol, propylene glycol or glycerine, or esters of fatty alcohols with alkane acids of low carbon number or with fatty acids; alkyl benzoates; silicone oils, such as dimethylpolysiloxanes, diethylpolysiloxanes, diphenylpolysiloxanes, and mixtures thereof.

The oil phase of the emulsions, oleogels or hydrodispersions or lipodispersions within the scope of the present invention is advantageously selected from the group of esters of saturated and/or unsaturated, branched and/or unbranched alkane carboxylic acids of chain length from 3 to 30 carbon atoms and saturated and/or unsaturated, branched and/or unbranched alcohols of chain length from 3 to 30 carbon atoms, from the group of esters from aromatic carboxylic acids and saturated and/or unsaturated, branched and/or unbranched alcohols of chain length from 3 to 30 carbon atoms. Such ester oils can include isopropyl myristate, isopropyl palmitate, isopropyl stearate, isopropyl oleate, n-butyl stearate, n-hexyl laurate, n-decyloleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semisynthetic, and natural or synthetic mixtures of such esters, for example, jojoba oil.

Furthermore, the oil phase can advantageously be selected from the group of branched and unbranched hydrocarbons and waxes, silicone oils, dialkyl ethers, the group of saturated or unsaturated, branched or unbranched alcohols, and fatty acid triglycerides, namely the triglycerine esters of saturated and/or unsaturated, branched and/or unbranched alkane carboxylic acids of chain length from 8 to 24, in particular 12-18, carbon atoms. The fatty acid triglycerides can advantageously be selected, for example from the group of synthetic, semi-synthetic and natural oils, for example olive oil, sunflower oil, soybean oil, peanut oil, rape-seed oil, almond oil, palm oil, coconut oil, palm kernel oil, pumpkin seed oil, avocado oil, and the like.

Also any mixtures of such oil and wax components can be used advantageously within the scope of the present invention. It can also optionally be advantageous to use waxes, for example cetyl palmitate, as the single lipid component of the oil phase.

The oil phase advantageously can include 2-ethylhexyl isostearate, octyl-5-dodecanol, isotridecyl isononanoate, isoeicosane, 2-ethylhexyl cocoate, $C_{12-15}$ alkyl benzoate, capryl-capric acid triglyceride, and/or dicaprylyl ether.

Mixtures of $C_{12-15}$ alkyl benzoate and 2-ethylhexyl isostearate, mixtures of $C_{12-15}$ alkyl benzoate and isotridecyl isononanoate and mixtures of $C_{12-15}$ alkyl benzoate, 2-ethylhexyl isostearate, and isotridecyl isononanoate are particularly advantageous. Of the hydrocarbons, paraffin oil, squalane, and squalene can be used advantageously within the scope of the present invention.

The oil phase can advantageously also contain cyclic or linear silicone oils or can consist completely of such oils, but wherein it is preferable, apart from the silicone oil or the silicone oils, to use an additional amount of other oil phase components. Cyclomethicone (octamethylcyclotetrasiloxane) is advantageously employed as silicone oil to be used according to the invention. However, other silicone oils should also advantageously be used within the scope of the present invention, for example hexamethylcyclotrisiloxane, polydimethylsiloxane, poly(methylphenylsiloxane). Mixtures of cyclomethicone and isotridecyl isononanoate, of cyclomethicone and 2-20 ethylhexyl isostearate, are also particularly advantageous.

The aqueous phase of the compositions of the invention can optionally contain advantageously alcohols, diols, or polyols of low C number, and their ethers, preferably ethanol, isopropanol, propylene glycol, glycerine, ethylene glycol, ethylene glycol monoethyl or monobutyl ether, propylene glycol monomethyl, monoethyl or monobutyl ether, diethylene glycol monomethyl or monoethyl ether, and analogous products, also alcohols of low C number, for example ethanol, isopropanol, 1,2-propane diol, glycerine and, in particular, one or more thickening agents, which can advantageously be selected from silicon dioxide, aluminum silicates, polysaccharides, or their derivatives, for example hyaluronic acid, xanthan gum, hydroxypropylmethylcellulose, and particularly advantageously from polyacrylates, in each case individually or in combination.

Mixtures of the above-mentioned solvents are used in particular. For alcoholic solvents, water can be a further constituent.

Gels within the scope of the invention generally contain alcohols of low C number, for example ethanol, isopropanol, 1,2-propane diol, glycerine, and water, or an above-mentioned oil in the presence of a thickening agent, which for oily-alcoholic gels is preferably silicon dioxide or an aluminum silicate, for aqueous-alcoholic or alcoholic gels is preferably a polyacrylate.

The conventionally-known, highly volatile, liquefied propellants, for example hydrocarbons (propane, butane, isobutane), which can be used alone or mixed with one another, are suitable as propellants for compositions which can be sprayed from aerosol containers according to the present invention. Compressed air can also advantageously be used.

Cosmetic compositions of the invention which are a skin-cleansing agent or shampooing agent preferably contain at least one anionic, non-ionic or amphoteric surfactant substance, or also mixtures of such substances. A botanical antioxidant blend of the invention in aqueous medium and auxiliaries, as are used conventionally therefore. The surfactant substance or the mixtures of these substances can be present in the shampooing agent in a concentration between 1 wt % and 50 wt %.

These cosmetic or dermatological compositions can also be aerosols having the auxiliaries conventionally used therefor.

Aqueous cosmetic cleansing agents of the invention or low-water or anhydrous cleansing agent concentrates intended for aqueous cleansing can contain anionic, non-ionic and/or amphoteric surfactants, for example traditional soaps, for example fatty acid salts of sodium alkyl sulfates, alkyl ether sulfates, alkane and alkyl benzene sulfonates, sulfoacetates, sulfobetaines, sarcosinates, amidosulfobetaines, sulfosuccinates, sulfosuccinic acid semiesters, alkyl ether carboxylates, protein-fatty acid condensates, alkylbetaines and amidobetaines, fatty acid alkanol amides, or polyglycol ether derivatives.

Compositions of the invention which are cosmetic cleansing compositions for the skin, can be present in liquid or solid form. In addition to a botanical antioxidant blend of the invention, they preferably contain at least 5 one anionic, non-ionic or amphoteric surfactant substance or mixtures thereof, if required one or more electrolytes and auxiliaries, as are used conventionally therefor. The surfactant substance can be present in the cleansing compositions in a concentration between 0.001 and 99.999 wt %, based on the total weight of the compositions.

Compositions of the invention which are a shampooing agent, in addition to a effective amount of a botanical antioxidant blend of the invention, preferably contain an anionic, non-anionic or amphoteric surfactant substance or mixture thereof, optionally an electrolyte of the invention and auxiliaries, as are used conventionally therefor. The surfactant substance can be present in the shampooing agent in a concentration between 0.001 wt % and 99.999 wt %.

Inventive compositions may contain, apart from the aforementioned surfactants, water and optionally the additives which are conventional in cosmetics, for example perfume, thickener, dyestuffs, deodorants, antimicrobial materials, back-fatting agents, complexing and sequestering agents, pearlescent agents, plant extracts, vitamins and/or their derivatives, active ingredients, and the like.

The invention will be further illustrated by selected examples, which are not meant to limit this invention to the particular materials, conditions, and products described.

Example 1

Retinol ($C_{20}H_{30}O$, 286.45 g/mol) can be converted to retinal ($C_{20}H_{28}O$, 284.44 g/mol) according to the following protocol:

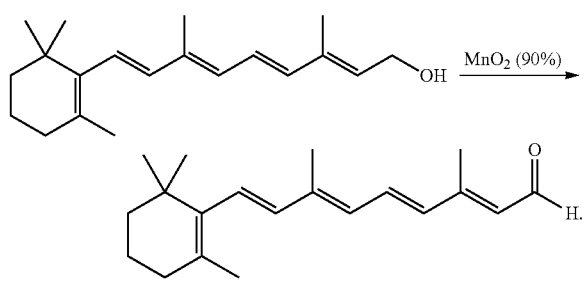

Example 2

Retinal ($C_{20}H_{28}O$, 284.44 g/mol) can be converted to retinoic acid ($C_{20}H_{28}O_2$, 300.44 g/mol) according to the following protocol:

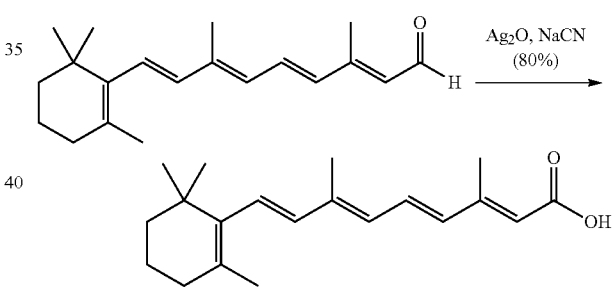

Example 3

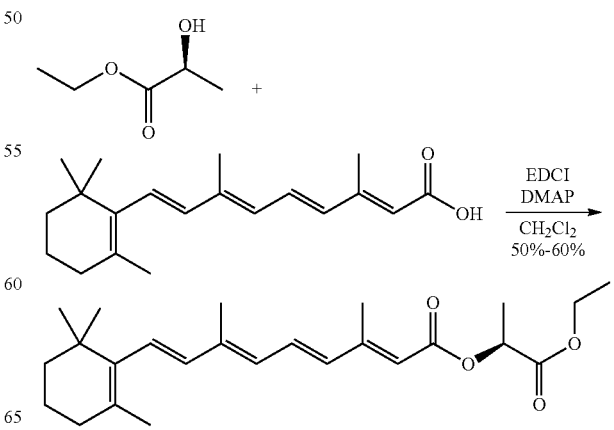

Under inert conditions, a slurry of retinoic acid ($C_{20}H_{28}O_2$, 300.44 g/mol, 50.0 g, 0.166 mol) in dichloromethane (500 mL) was stirred. To the slurry were added (−)-ethyl L-lactate ($C_5H_{10}O_3$, 118.13 g/mol, 1.03 g/cm$^3$, 22.6 mL, 0.20 mol), followed by N,N-dimethylaminopyridine (DMAP, $C_7H_{10}N_2$, 122.17 g/mol, 4.1 g, 0.033 mol) at ambient temperature, and then, on an ice-water bath at about 5° C., 1-ethyl-3-(3-dimethylaminopropyl)carbodiimide (EDCI, $C_8H_{12}N_3$, 155.24 g/mol, 38.3 g, 0.20 mol). The reaction mixture was allowed to warm up to ambient temperature over 3-4 h and stirred at ambient temperature for 15-16 h. The reaction (amber color homogeneous mixture) was quenched with water (400 mL) and transferred into a separatory funnel. The organic layer was separated, washed with water (400 mL), saturated sodium chloride solution (400 mL×2), and dried over sodium sulfate. The filtrate was concentrated under reduced pressure to obtain 78 g of a crude oil. After column chromatography (Biotage, KP-Sil) with 1% acetone in hexanes, 40.7 g of ethyl lactate retinoate were isolated as a yellow oil ($C_{25}H_{36}O_4$, 400.55 g/mol, 0.102 mol, 61.2%) in 97.8% purity. $^1$H-NMR (chloroform-d): 1.03 (s, 6H); 1.28 (t, 3H); 1.47 (m, 1H); 1.49 (br d, 2H); 1.53 (br d, 2H); 1.62 (m, 2H); 1.72 (s, 3H); 2.00 (s, 3H); 2.03 (m, 2H); 2.36 (s, 3H); 4.22 (q, 2H); 5.11 (q, 1H); 5.86 (s, 1H); 6.12 (d, 1H); 6.16 (d, 1H); 6.26 (d, 1H); 6.29 (d, 1H); 7.02 (dod, 1H). $^{13}$C-NMR (chloroform-d): 13.11, 14.18, 14.30, 17.27, 19.40, 21.94, 29.15, 33.30, 34.43, 39.77, 61.47, 68.27, 117.54, 129.04, 129.65, 130.26, 131.70, 135.10, 137.42, 137.85, 140.14, 154.51, 166.42, 171.44.

Example 4

A group of 26 subjects were tested to compare the activity of lactic acid retinoate (single conjugate) with ethyl lactate retinoate (double conjugate). As a general protocol, a patch (Webril cotton with 0.05 ml of a 5.0% aqueous solution) was applied to the upper outer arm or back of each subject. The entire test was composed of (1) an induction phase (2) a rest phase and (3) a challenge phase.

The scoring scale was as follows:
0=not sensitized;
1=mild sensitization (viz. erythema and a little edema);
2=moderate sensitization (erythema with infiltration, raised, spreading beyond the borders of the patch, with or without vesiculation); and
3=strong sensitization (large vesicula-bullous reaction).

For the double conjugate, ethyl lactate retinoate, 0% of the sample population had any skin irritation or allergic reactions. For the single conjugate, lactyl retinoate, many subjects had skin irritation sufficient enough to change protocol application and 4% of the sample population had a delayed skin irritation reaction presumptive of contact allergy. From the above it can be seen that the use of a double conjugate according to the invention in place of a single conjugate, leads to surprisingly less skin irritation and allergic response in human populations.

While the invention has been illustrated and described in detail in the foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B, and C" should be

TABLE 1

Maximization Assays

| LACTYL RETINOATE | ETHYL LACTATE RETINOATE |
|---|---|
| Number of Subjects: 26 | Number of Subjects: 26 |
| Method: The patch was applied to the upper outer arm or back of each subject. The entire test was composed of (1) a Induction phase (2) a Rest phase and (3) a Challenge phase | |
| Method Deviation: In several panelists, the induction patch had to be moved to nearby areas several times because of the moderate to severe irritation that was observed. In view of these reactions, it was necessary to eliminate further SLS applications and only use the test product following the third induction exposure. | Method Deviation: None Required |
| Results: One subject dropped out unrelated to study product; 25 panelists completed this investigation, as outlined in the standard protocol with the protocol deviation noted. No adverse or unexpected reactions were seen in any of the panelists during the induction phase. One volunteer developed a raised erythematous reaction without vesiculation at 48 hours (score 1) that persisted at 72 hours (score 2). | Results: There were no protocol deviations. No adverse or unexpected reactions were seen in any of the panelists during the induction phase. The results of the challenge are shown below. No instances of contact allergy were recorded at either 48 or 72 hours after the application of the challenge patches. |
| Maximization Testing Results: Product coded #RD 04-011 - Face Cream (tested as supplied) Subject Number: 01-24, 48-Hour Grading: 0 Subject Number: 01-24, 72-Hour Grading: 0 Subject Number: 26, 48-Hour Grading: 1 Subject Number: 26, 72-Hour Grading: 2 | Maximization Testing Results: Subject Number: 01-26, 48-Hour Grading: 0 Subject Number: 01-26, 72-Hour Grading: 0 |

The invention claimed is:

1. A method of treating a skin condition in a human, comprising:
   contacting the skin of the human in need of such treatment with an effective amount of a composition comprising the molecule of formula (Id),

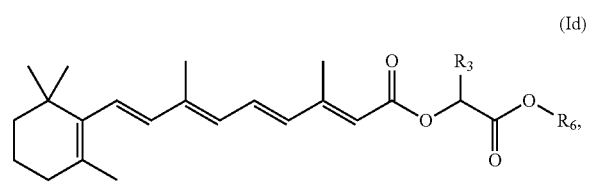

wherein
   $R_3$ is H or alkyl consisting of 1 carbon atom, and
   $R_6$ is alkyl consisting of 1, 2, 3, or 4 carbon atoms; and
   wherein the skin condition is acne, photodamage, fine lines and wrinkles, or a combination thereof.

2. The method of claim 1, wherein the composition further comprises:
   a carrier; and
   0.01 to 0.5 wt %, relative to the total weight of the composition, of the molecule of formula Id.

3. The method of claim 1, wherein the composition further comprises:
   an α-hydroxy acid.

4. The method of claim 1, wherein the molecule has the formula (If)

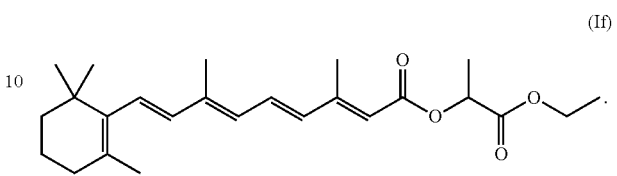

5. The method of claim 1, wherein the molecule has the formula (Ig)

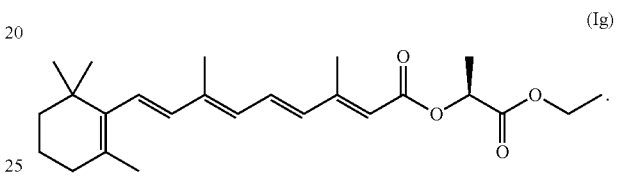

6. The method of claim 1, wherein the molecule of formula (Id) is present in an amount of 0.01 to 0.25 wt %.

7. The method of claim 1, wherein the molecule of formula (Id) is present in an amount of 0.01 to less than 0.2 wt %.

8. The method of claim 1, wherein the molecule of formula (Id) is present in the amount of 0.02 to 0.175 wt %.